US00PP30413P3

(12) United States Plant Patent
Stemkens

(10) Patent No.: US PP30,413 P3
(45) Date of Patent: Apr. 16, 2019

(54) *LAVANDULA* PLANT NAMED 'LAAZ0006'

(50) Latin Name: *Lavandula angustifolia*
Varietal Denomination: LAAZ0006

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,648

(22) Filed: Jul. 12, 2017

(65) Prior Publication Data

US 2019/0021205 P1 Jan. 17, 2019

(51) Int. Cl.
*A01H 5/02* (2018.01)

(52) U.S. Cl.
USPC ..... Plt./445

(58) Field of Classification Search
USPC ..... Plt./445
See application file for complete search history.

*Primary Examiner* — Keith O. Robinson
(74) *Attorney, Agent, or Firm* — Dale Skalla

(57) ABSTRACT

A new *Lavandula* plant named 'LAAZ0006' particularly distinguished by purple-blue flowers, a very long flowering season, dark green foliage with a bit greyish hue, about large sized plants with a well-branched, relatively tight and upright habit. The plant is very resistant to cold.

1 Drawing Sheet

Figure 1:
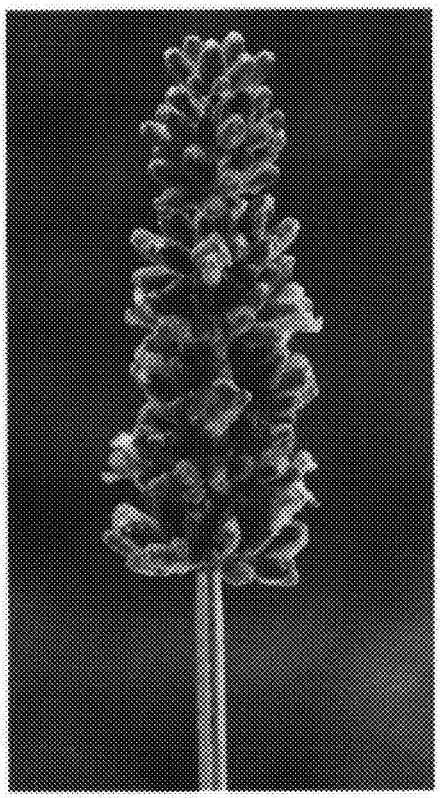

Latin name of the genus and species of the plant claimed: *Lavandula angustifolia.*

Varietal denomination: 'LAAZ0006'.

BACKGROUND OF THE NEW PLANT

The present invention comprises a new *Lavandula*, botanically known as *Lavandula angustifolia*, and hereinafter referred to by the variety name 'LAAZ0006'.

'LAAZ0006' is a product of a planned breeding program. The new cultivar has purple-blue flowers, a very long flowering season, dark green foliage with a bit greyish hue, about large sized plants with a well-branched, relatively tight and upright habit. The plant is very resistant to cold.

'LAAZ0006' originated from a pollination made in July 2011 in a greenhouse in Enkhuizen, Netherlands.

The female parent was the unpatented, proprietary plant designated 'N4235-1', with blue violet flowers, a more mounding habit, very grey foliage and flowering 12 days earlier when compared to 'LAAZ0006'.

The male parent of 'LAAZ0006' is unknown.

The resultant seed was sown in January 2012 and grown outdoors in Enkhuizen, Netherlands. 'LAAZ0006' was selected as a single flowering plant within the progeny of the stated cross on June 22 in Enkhuizen, Netherlands.

The first act of asexual reproduction of 'LAAZ0006' was accomplished when stem tip vegetative cuttings were propagated from the initial selection July 2012 in a greenhouse in Enkhuizen, Netherlands.

BRIEF SUMMARY OF INVENTION

Horticultural examination of plants grown from cuttings of the plant initiated in July 2012, and continuing thereafter, has demonstrated that the combination of characteristics as herein disclosed for 'LAAZ0006' are firmly fixed and are retained through successive generations of asexual reproduction.

'LAAZ0006' has not been observed under all possible environmental conditions. The phenotype may vary significantly with variations in environment such as temperature, light intensity and day length.

A Plant Breeder's Right for this cultivar was applied for in the European Union on Aug. 2, 2016, No. 2016/1897. 'LAAZ0006' has not been made publicly available prior to the effective filing date of this application, notwithstanding any disclosure that may have been made less than one year prior to the effective filing date of this application by the inventor or another who obtained 'LAAZ0006' directly from the inventor.

The following traits have been repeatedly observed and are determined to be basic characteristics of the new variety. The combination of these characteristics distinguishes this *Lavandula* as a new and distinct variety.

BRIEF DESCRIPTION OF THE PHOTOGRAPHS

The accompanying photographic drawings show typical flower and foliage characteristics of 'LAAZ0006' with colors being as true as possible with an illustration of this type. The photographic drawings show in FIG. 1 a close view of an inflorescence and in FIG. 2 a whole flowering plant from an outdoor trial.

DETAILED BOTANICAL DESCRIPTION

The plant descriptions and measurements were taken outdoors in Enkhuizen, Netherlands on Jun. 16, 2017 on about 23 week old plants. Rooted cuttings had been planted, one plant per pot, in 13 cm pots in week 35, 2016. The plants were pinched.

Figure 2:
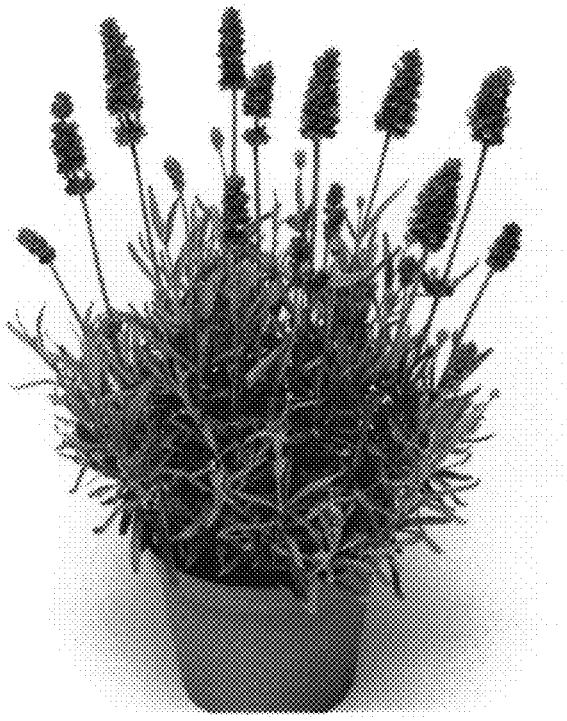

The aforementioned photographs: FIGS. 1 and 2 were taken in Gilroy, Calif. Jun. 29, 2017, and using an about 12 week old plant in a 13 cm pot from an outdoor trial.

Color references are made to The Royal Horticultural Society Colour Chart (R.H.S.) 2001.

TABLE 1

DIFFERENCES BETWEEN THE NEW VARIETY 'LAAZ0006' AND A MOST SIMILAR VARIETY

| | 'LAAZ0006' | 'LAAZ0005' (U.S. Plant Pat. No. 27,477) |
|---|---|---|
| Flowering response: | Earlier by about 2 weeks | Start of flowering later |
| Cold resistance: | Very good | Good |
| Length of peduncle: | Up to 12 cm | Up to 7 cm |

Plant:

*Form, growth and habit.*—Compact, upright, freely branching.

*Plant height.*—19.0-24.0 cm.

*Plant height (inflorescence included).*—About 29.5 cm.

*Plant width.*—About 42.0 cm.

Roots:

*Number of days to initiate roots.*—About 13 days at about 20 degrees C.

*Number of days to produce a rooted cutting.*—4-5 weeks at 18 degrees C.

*Type.*—Fine, fibrous, free branching.

*Color.*—Closest RHS 155D.

Foliage:

*Type.*—Opposite; decussate, sessile.

*Fragrance.*—Strong Lavender.

*Immature, leaf color, upper surface.*—RHS 137A.

*Lower surface.*—RHS 137C.

*Mature, leaf color, upper surface.*—RHS 138A.

*Lower surface.*—RHS 139C.

*Length.*—2.5-3.4 cm.

*Width.*—0.8 cm.

*Shape.*—Ligulate.

*Base shape.*—Sessile.

*Apex shape.*—Acute.

*Margin.*—Entire.

*Texture, upper surface.*—Pubescent.

*Lower surface.*—Pubescent.

*Color of veins, upper surface.*—RHS 143C.

*Color of veins, lower surface.*—RHS 143C.

Stem:

*Number of main stems per plant.*—About 15-22.

*Color of stem.*—RHS N138A.

*Length of stem.*—About 17.0-20.0 cm.

*Diameter.*—0.3 cm.

*Length of internodes.*—2.5-4.5 cm.

*Shape of stem.*—Square.

*Strength.*—Good.

*Texture.*—Pubescent.

*Peduncle color.*—RHS N138B.

*Peduncle length.*—About 12.0 cm.

*Peduncle diameter.*—0.2 cm.

*Peduncle strength.*—Strong.

*Peduncle texture.*—Pubescent.

Inflorescence:

*Flowering season.*—From June until October.

*Type.*—Flowers in compact spikes, terminal on stems; flowers stay open all day.

*Number of open flowers per inflorescence.*—About 115 in various stages of development.

*Quantity of inflorescences per plant.*—About 24-36.

*Lastingness of individual blooms on the plant.*—About 4 days.

Bud (when first showing color):

*Color.*—RHS 90B.

*Length.*—0.4 cm.

*Width.*—0.3 cm.

*Shape.*—Oval.

Corolla:

*Immature, color of petals, upper surface.*—RHS 90C.

*Immature, color of petals, lower surface.*—RHS 90C.

*Spike horizontal diameter.*—2.3 cm.

*Spike height.*—6 cm.

*Mature, color of petals, upper surface.*—RHS 93B.

*Mature, color of petals, lower surface.*—RHS 93B.

*Petal length.*—0.2 cm.

*Petal diameter.*—0.2 cm.

*Apex.*—Obtuse.

*Margin.*—Entire.

*Shape.*—Rounded.

*Base.*—Fused.

*Degree of lobation.*—Moderate.

*Texture, upper surface.*—Glabrous.

*Texture, lower surface.*—Glabrous.

*Corolla tube, color, outer surface.*—RHS 84B and RHS N155B.

*Corolla tube, color, inner surface.*—RHS 84B and RHS N155B.

*Corolla tube length.*—0.3 cm.

*Diameter (at opening).*—0.2 cm.

*Corolla tube texture, outer surface.*—Glabrous.

*Corolla tube texture, inner surface.*—Glabrous.

Calyx:

*Form.*—All sepals fused to form tube around the corolla.

*Color.*—RHS N88A.

*Length of tube.*—0.3 cm.

*Width of tube.*—0.2 cm.

*Texture, outer surface.*—Pubescent.

*Texture, inner surface.*—Glabrous.

Reproductive organs:

*Number of stamens.*—4.

*Filament color.*—RHS 155C.

*Filament length.*—0.2 cm.

*Filament diameter.*—0.05 cm.

*Anther color.*—RHS N167A.

*Anther length.*—0.05 cm.

*Anther shape.*—Reniform.

*Pollen color.*—RHS 163B.

*Pollen amount.*—Sparse.

*Pistil.*—1 per flower.

*Pistil length (cm).*—0.4 cm.

*Style color.*—RHS 150D.

*Style length.*—0.2 cm.

*Stigma color.*—RHS N199C.

Fertility/seed set: Has not been observed to date.

Disease/pest resistance: Has not been observed to date.

What is claimed is:

1. A new and distinct cultivar of *Lavandula* plant named 'LAAZ0006', as substantially illustrated and described herein.

* * * * *